United States Patent
Horiuchi et al.

[11] Patent Number: 5,878,160
[45] Date of Patent: Mar. 2, 1999

[54] FLOW TYPE PARTICLE IMAGE ANALYZING METHOD AND APPARATUS FOR DISPLAYING PARTICLE IMAGES BY CLASSIFYING THEM BASED ON THEIR CONFIGURATIONAL FEATURES

[75] Inventors: Hideyuki Horiuchi, Abiko; Hideki Asai, Mito; Yasuaki Kojima; Norio Oowada, both of Hitachinaka; Kazuhiro Sano, Naka-machi, all of Japan

[73] Assignee: Hitachi, Ltd., Tokyo, Japan

[21] Appl. No.: 589,102

[22] Filed: Jan. 23, 1996

[30] Foreign Application Priority Data

Feb. 1, 1995  [JP]  Japan ................................. 7-014910

[51] Int. Cl.$^6$ ........................................ G06K 9/78
[52] U.S. Cl. ........................ 382/133; 382/224; 702/21
[58] Field of Search ........................ 382/133, 134, 382/128, 224, 225, 203, 309, 311; 364/555; 702/21

[56] References Cited

U.S. PATENT DOCUMENTS

| | | | |
|---|---|---|---|
| 4,338,024 | 7/1982 | Bolz et al. | 356/23 |
| 4,573,196 | 2/1986 | Crane et al. | 382/185 |
| 4,612,614 | 9/1986 | Deindoerfer et al. | 356/335 |
| 4,718,102 | 1/1988 | Crane et al. | 382/185 |
| 5,235,522 | 8/1993 | Bacus | 364/497 |
| 5,287,272 | 2/1994 | Rutenberg et al. | 382/224 |
| 5,319,721 | 6/1994 | Chefalas et al. | 382/160 |
| 5,677,966 | 10/1997 | Doerrer et al. | 382/128 |
| 5,715,182 | 2/1998 | Asai et al. | 364/555 |

FOREIGN PATENT DOCUMENTS

| | | |
|---|---|---|
| A0549 905 | 1/1992 | European Pat. Off. . |
| 63-94156 | 4/1988 | Japan . |
| 3-105235 | 5/1991 | Japan . |
| 4-72544 | 3/1992 | Japan . |
| 4-309841 | 11/1992 | Japan . |
| 7-20124 | 1/1995 | Japan . |
| WO91/15826 | 10/1991 | WIPO . |

*Primary Examiner*—Jon Chang
*Attorney, Agent, or Firm*—Fay, Sharpe, Beall, Fagan, Minnich & McKee

[57] ABSTRACT

A flow type particle image analytical method for feeding a particles-suspended sample by surrounding it by a cleaning solution, imaging particles in the sample by irradiating light to it, and automatically classifying the particles in the sample by analyzing the picked-up particle images, wherein the method comprises a means for designating the kind of particles to be reviewed beforehand among the classified particles, a means for storing only particles which are automatically classified to the designated particle kind in a review image memory, a means for displaying particles of the same kind on a CRT display in batch so as to review particle images, and a means for classifying each of the displayed particles finally by an operator or for changing the particle name.

8 Claims, 5 Drawing Sheets

FLOW TYPE PARTICLE IMAGE ANALYZING METHOD AND APPARATUS FOR DISPLAYING PARTICLE IMAGES BY CLASSIFYING THEM BASED ON THEIR CONFIGURATIONAL FEATURES

BACKGROUND OF THE INVENTION

The present invention relates to a flow type particle image analytical method and apparatus for generating an image of particles in a sample, which form a suspended flow of the sample, by irradiating light to the formed sample flow and automatically classifying the particles in the sample by analyzing the generated particle image, and particularly to a flow type particle image analytical method and apparatus suited to classify and display the particle image based on configurational features such as configuration, size or color of the particle image according to biological kinds of particles such as cells in blood or urine.

To conventionally classify and analyze particles such as cells in blood or cells existing in urine, a sample is prepared on a glass slide sheet and observed with a microscope. In the case of urine, the particle concentration in the urine is thin, so that a measuring sample is centrifugalized and concentrated by a centrifuge beforehand and then observed. In an apparatus for automating these observation and examination work, a sample of blood or other material is coated on a glass slide and set in a microscope, and the microscope stage is automatically scanned and stopped at a position where particles exist. A still image of particles then is picked up and particles in the sample are classified by using a characteristic extraction and pattern recognition method by the image processing art.

However, in the aforementioned method, it takes a lot of time to prepare a sample and an operation for finding a particle by moving the microscope stage mechanically and moving the particle into a suitable image fetching area is required. As a result, problems arise in that the analysis requires a lot of time and the mechanism is complicated.

To realize high precise examination and labor saving, there is a flow type particle image analytical apparatus using a flow cell for using a sheath solution which has a cleaning solution as an outer layer and controlling the sample solution to an extremely flat flow which is disclosed in, for example, U.S. Pat. No. 4,338,024, Japanese Patent Application Laid-Open 63-94156, and Japanese Patent Application Laid-Open 4-72544.

In the flow type particle image analytical apparatus, a sample moving in a flow cell is imaged, for example, by a video camera and the particles in the sample are classified and counted by processing the picked-up still image.

As a flow type particle image analytical apparatus for imaging particles in a sample by changing the magnification, a particle analytical apparatus is described in Japanese Patent Application Laid-Open 3-105235 and Japanese Patent Application Laid-Open 4-309841.

The flow type particle analytical apparatus described in Japanese Patent Application Laid-Open 3-105235 and Japanese Patent Application Laid-Open 4-309841 mentioned above comprises a stroboscope continuously emitting light having a short emission time, a stop for adjusting the quantity of the stroboscopic light, a diffusion plate for eliminating variations in the quantity of stroboscopic light, a condenser lens for focusing the stroboscopic light, a flow cell which is arranged in the position where the stroboscopic light passes and lets a sample flow flat by surrounding the sample by a sheath solution, an object lens for forming an image of a particle irradiated by the stroboscopic light, a high-powered projection lens, a low-powered projection lens, a TV camera for picking up an image, a means for moving the diffusion plate, a means for changing the aperture stop, and a switching means for switching the high-powered projection lens and low-powered projection lens.

A method for classifying a particle image formed by the aforementioned flow type particle image analytical apparatus by the particle size and displaying it on a CRT screen and classifying particles by an operator is proposed in U.S. Pat. No. 4,612,614.

However, there is the following problem imposed in the flow type particle image analytical apparatus described in U.S. Pat. No. 4,612,614 mentioned above.

Namely, it is premised in the flow type particle image analytical apparatus that the particle classification work is reviewed by an operator by watching an image on the CRT and an extremely large image memory is necessary so as to analyze all particles in a sample. Particularly in a sample having a large particle concentration, all particles cannot be stored in a limited image memory and furthermore it requires a lot of time for an operator to proceed with the classification work by watching images. When the image memory is not sufficient, the number of particles to be reviewed decreases and it is difficult to expect a reproducible classification result.

SUMMARY OF THE INVENTION

An object of the present invention is to provide a flow type particle image analytical method and apparatus suited to realization of a small-capacity image memory and prevention of reduction in the reproducibility of the classification result.

The problem solving means so as to accomplish the object of the present invention are as follows:

1. A flow type particle image analytical method characterized in that the method forms a flow of a particles-suspended sample, generates an image of particles in the sample by irradiating light to the formed sample flow, and automatically classifies the particles in the sample by analyzing the generated particle image, wherein the method designates the kind of particles to be reviewed, controls storage of an image in a review image memory so as to store an image of particles corresponding to the designated particle kind in the review image memory, and displays the stored particle image on the display for review (Claim 1).

2. A flow type particle image analytical method of the solution means of 1 characterized in that the aforementioned particle image display is given in batch for each particle kind (Claim 2).

3. A flow type particle image analytical method of the solution means of 1 characterized in that the aforementioned particle kind designation is made for one sample in each measuring mode (Claim 3).

4. A flow type particle image analytical apparatus characterized in that the apparatus forms a flow of a particles-suspended sample, generates an image of particles in the sample by irradiating light to the formed sample flow, and automatically classifies the particles in the sample by analyzing the generated particle image, wherein the apparatus comprises a means for designating the kind of particles to be reviewed, a review image memory, a means for controlling storage of an image in the review image memory so as to store an image of particles corresponding to the designated particle kind in the review image memory, and a means for displaying the stored particle image for review (Claim 4).
5. A flow type particle image analytical apparatus of the solution means of 4 characterized in that the aforementioned image storage control means includes a means for turning storage of an image of particles which cannot be classified on or off and is structured so as to store the image of particles which cannot be classified in the review image memory when the image storage ON/OFF means is in the ON state (Claim 5).
6. A flow type particle image analytical apparatus of the solution means of 4 characterized in that the apparatus has a means for registering a specific particle kind beforehand and the aforementioned image storage control means includes a means for turning storage of an image of particles corresponding to the specific particle kind on or off and is structured so as to store an image of particles which correspond to the registered specific particle kind and are automatically classified in the review image memory when the image storage ON/OFF means is in the ON state (Claim 6).
7. A flow type particle image analytical apparatus of the solution means of 4 characterized in that the aforementioned image storage control means includes a means for turning storage of an image of ambiguous particles which are considered to correspond to the particle kind of the first candidate but are considered to possibly correspond to the particle kind of the second candidate close to the particle kind of the first candidate on or off and is structured so as to store the image of ambiguous particles in the review image memory when the image storage ON/OFF means is in the ON state and the aforementioned display means is structured so as to display the particle kinds of both the candidates in addition to the image of ambiguous particles which is stored as an image relating to the particle kinds of both the candidates (Claim 7).
8. A flow type particle image analytical apparatus of the solution means of 4 characterized in that the aforementioned image storage control means includes a means for turning storage of an image of particles on or off and is structured so as to store an image of particles corresponding to another particle kind which is apt to be misdecided as one corresponding to the designated particle kind by automatic classification in the review image memory when the image storage ON/OFF means is in the ON state and the aforementioned display means is structured so as to display the image of particles corresponding to the designated particle kind and the image of particles corresponding to the another particle kind for comparison observation (Claim 8).
9. A flow type particle image analytical apparatus of the solution means of 4 characterized in that the apparatus is structured so that an operator classifies particles displayed on the display unit finally or changes the particle kind name and furthermore corrects the automatic classification result of particles which are automatically classified on the basis of the aforementioned classification result (Claim 9).
10. A flow type particle image analytical apparatus of the solution means of 9 characterized in that the apparatus is structured so that the automatic classification result of the automatically classified particles is corrected on the basis of the existence ratio of the particles which are objects of review for each corresponding particle kind (Claim 10).
11. A flow type particle image analytical apparatus of the solution means of 4 characterized in that the particles are cells of an organism (Claim 11).
12. A flow type particle image analytical apparatus of the solution means of 4 characterized in that the particles are blood corpuscles in blood (Claim 12).
13. A flow type particle image analytical apparatus of the solution means of 4 characterized in that the particles are sediment of urine (Claim 13).

The solution means of 1 designates the biological kind of particles to be reviewed, controls storage of an image in a review image memory so as to store an image of particles corresponding to the designated particle kind in the review image memory, and displays the stored particle image on the display for review. Therefore, according to this means, all generated particle images are not always stored in the review image memory, so that the memory capacity can be minimized and since there is no need to reduce the number of review particles to be stored originally regardless of it, the reproducibility of the classification result can be prevented from reduction.

The solution means of 2 displays particle images in batch for each biological particle kind. Therefore, according to this means, the review work can be simplified.

The solution means of 3 designates the particle kind for one sample in each measuring mode. Therefore, according to this means, useless particle images can be prevented from storage in the review image memory.

The solution means of 4 comprises a means for designating the particle kind to be reviewed, a review image memory, a means for removing images of particles corresponding to particle kinds other than the particle kind to be reviewed and controlling storage of an image in the review image memory so as to store an image of particles corresponding to the designated particle kind in the review image memory, and a means for displaying the stored particle image for review. Therefore, according to this means, in the same as with the solution means of 1, all particle images are not always stored in the review image memory, so that the memory capacity can be minimized and since there is no need to reduce the number of review particles to be stored originally regardless of it, the reproducibility of the classification result can be prevented from reduction.

In the solution means of 5, the image storage control means includes a means for turning storage of an image of particles which cannot be classified on or off and is structured so as to store the image of particles which cannot be classified in the review image memory when the image storage ON/OFF means is in the ON state. Therefore, according to this means, particles which cannot be classified by the apparatus can be classified by an operator.

The solution means of 6 has a means for registering a specific particle kind beforehand and the image storage control means includes a means for turning storage of an image of particles corresponding to the specific particle kind on or off and is structured so as to store an image of particles which correspond to the registered specific particle kind and are automatically classified in the review image memory when the image storage ON/OFF means is in the ON state. Therefore, according to this means, when, for example, particularly particles which are medically important are selected as a specific particle, these particles can be reviewed by an operator even if they are not designated one by one.

In the solution means of 7, the image storage control means includes a means for turning storage of an image of ambiguous particles which are considered to correspond to the particle kind of the first candidate but are considered to possibly correspond to the particle kind of the second candidate close to the particle kind of the first candidate on or off and is structured so as to store the image of ambiguous particles in the review image memory when the image storage ON/OFF means is in the ON state and the display means is structured so as to display the particle kinds of both the candidates in addition to the image of ambiguous particles which is stored as an image relating to the particle kinds of both the candidates. Therefore, according to this means, ambiguous particles which cannot be classified definitely by the apparatus can be classified efficiently by review by an operator.

In the solution means of 8, the image storage control means includes a means for turning storage of an image of particles on or off and is structured so as to store an image of particles corresponding to another particle kind which is apt to be misdecided as one corresponding to the designated particle kind by automatic classification in the review image memory when the image storage ON/OFF means is in the ON state and the display means is structured so as to display the image of particles corresponding to the designated particle kind and the image of particles corresponding to the another particle kind for comparison observation. Therefore, according to this means, particles which cannot be classified correctly by the apparatus can be classified efficiently by an operator.

The solution means of 9 is structured so that an operator classifies particles displayed on the display unit finally or changes the particle kind name and furthermore corrects the automatic classification result of particles which are automatically classified on the basis of the aforementioned classification result. Therefore, according to this means, the particle classification and discrimination precision can be improved.

The solution means of 10 is structured so that the automatic classification result of the automatically classified particles is corrected on the basis of the existence ratio of the particles which are objects of review for each corresponding particle kind. Therefore, according to this means, even if the capacity of the review image memory is insufficient, the particle classification and discrimination precision can be prevented from reduction due to it.

DETAILED DESCRIPTION OF THE PREFERRED EMBODIMENTS

Figure 1:
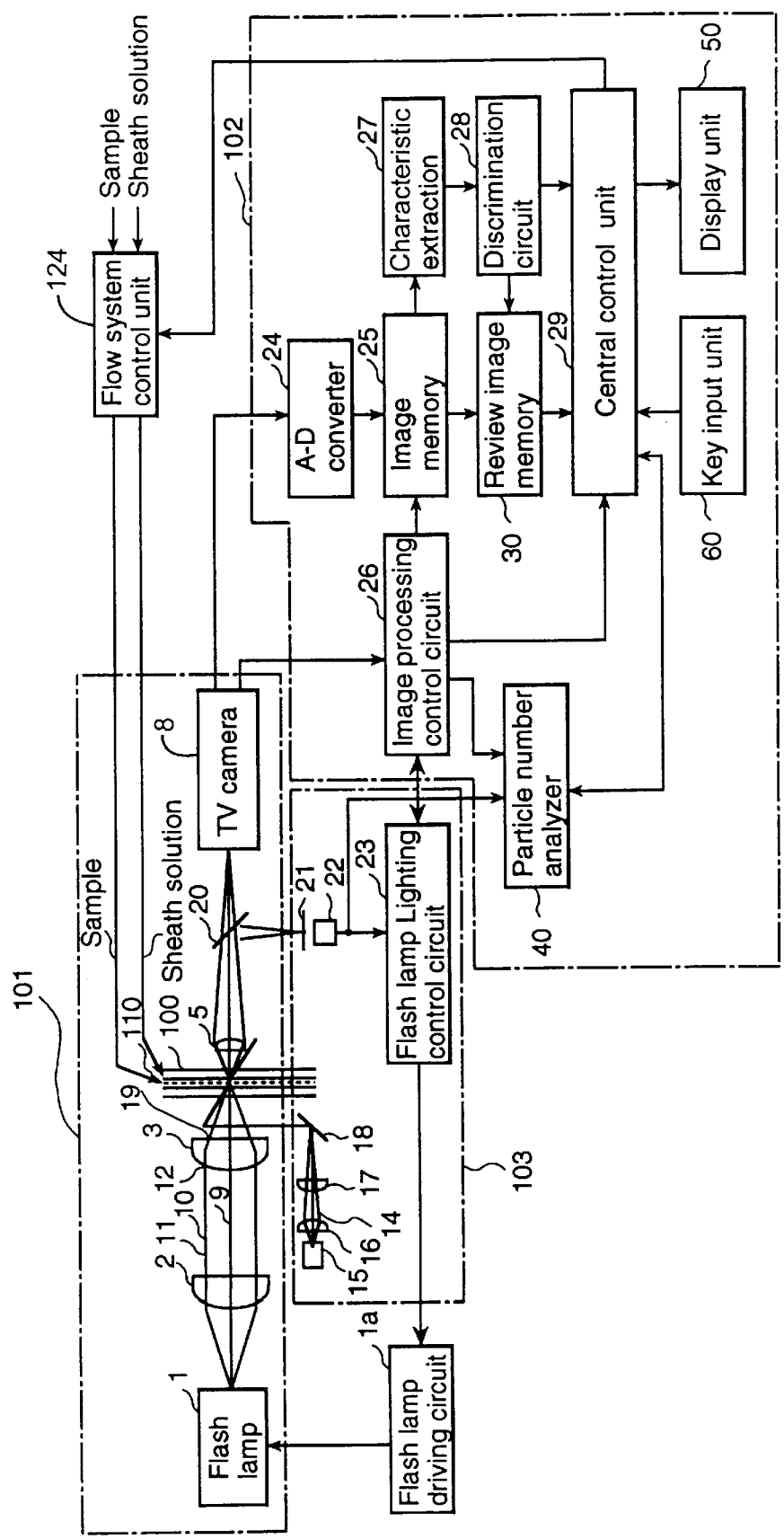
FIG. 1 is a whole block diagram of a flow type particle image analytical apparatus which is an embodiment of the present invention.

FIG. 1 is a whole schematic block diagram of a flow type particle image analytical apparatus which is an embodiment of the present invention. The flow type particle image analytical apparatus comprises a flow cell 100, an image pick-up device 101, a particle analyzer 102, a particle detector 103, and a flow system controller 124.

The image picking-up device 101 comprises a flash lamp driving circuit 1a, a flash lamp 1, a field lens 2, a view field stop 11, an aperture stop 12, a microscope condenser lens 3, a microscope object lens 5 (shared by the particle detector 103), and a TV camera 8. The particle analyzer 102 comprises an A-D converter 24, an image memory 25, an image processing control circuit 26, a characteristic extraction circuit 27, a discrimination circuit 28, a particle number analyzer 40, a central control unit 29, a review particle image memory 30, a display unit 50, and a key input unit 60.

Figure 2:
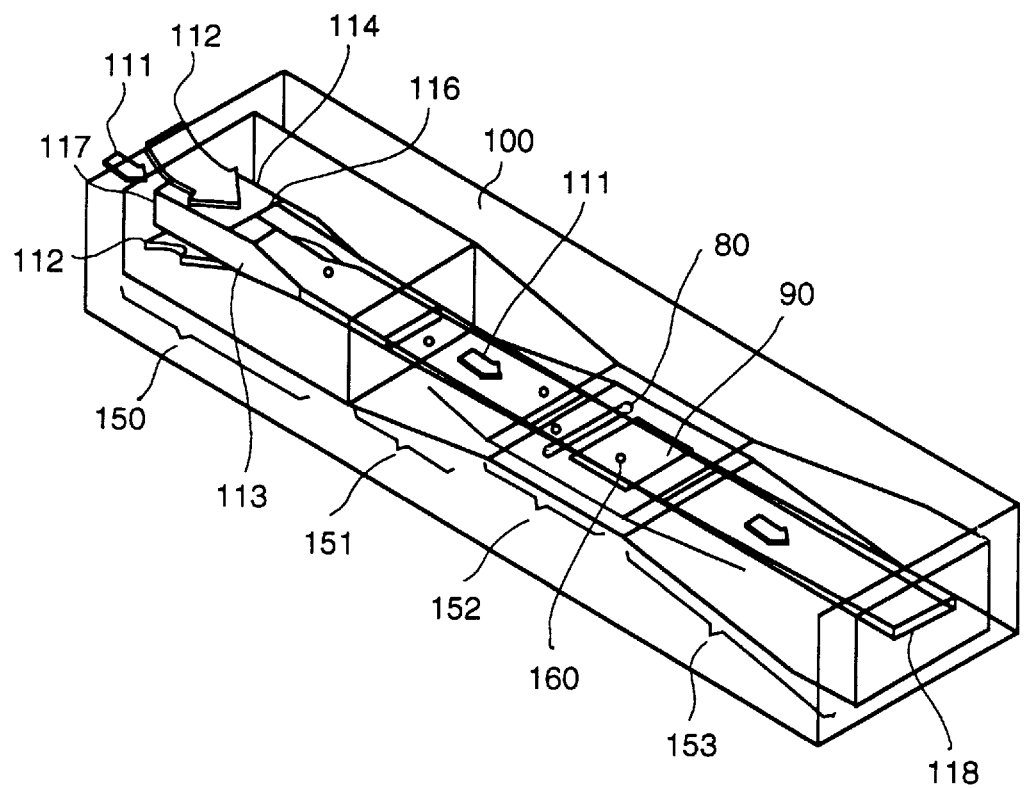
FIG. 2 is a perspective view showing the constitution of the flow cell shown in FIG. 1.

The flow cell 100 comprises, as shown in FIG. 2, a parallel flow path 150, a contraction flow path 151, a measurement flow path 152, and a deceleration flow path 153. The flow cell 100 is generally made of glass.

The cross section of the parallel flow path 150 perpendicular to a sample flow direction 111 between an inlet 117 and the junction portion with the contraction flow path 151 is quadrangular and a nozzle 114 is installed in the neighborhood of the inlet 117 of the parallel flow path 150.

The nozzle 114 has a cross section with a rectangular shape in which the thickness direction thereof which is almost the same as the passing direction of flashlight which will be described later is a short side and the width direction which is perpendicular to the thickness direction and the sample flow direction is a long side. The intersection point of the diagonal lines of the rectangle coincides with the intersection point of the diagonal lines of the quadrangle of the cross section of the inlet 117 of the parallel flow path 150 and the rectangle is contained inside the quadrangle. The inside of the nozzle 114 is a flow path of a sample and the outside thereof is a flow path of a sheath solution. Numeral 112 indicates a flow direction of a sheath solution.

The cross section of the nozzle 114 up to a nozzle outlet 116 in the sample flow direction 111 has a rectangular shape which is almost the same. A sample guide 113 is attached to the nozzle outlet 116 so as to keep the width of sample flow constant. The sample guide 113 comprises a pair of plates which face each other across the sample flow and is extended near the center of the parallel flow path 150 from the nozzle outlet 116.

The cross section of the contraction flow path 151 between the junction portion with the parallel flow path 150 and the junction portion with the measurement flow path 152 is quadrangular so that the size in the width direction is kept unchanged and the size in the thickness direction reduces slowly toward the measurement flow path 152.

The cross section of the measurement flow path 152 between the junction portion with the contraction flow path 151 and the junction portion with the deceleration flow path 153 has the same quadrangular shape and a particle detection area 80 and an image picking-up area 90 are installed at the center thereof.

The particle detection area 80 is extended in the width direction mentioned above and has a long and narrow shape having a length which is the same as the sample flow width. The image picking-up area 90 is arranged on the downstream side of the particle detection area 80 and has a quadrangular shape, one side of which has a length which is almost the same as the sample flow width.

The cross section of the deceleration flow path 153 between the junction portion with the measurement flow path 152 and an outlet 118 is quadrangular, and the size in the width direction is constant, and the size in the thickness direction enlarges slowly along the sample flow direction.

Next, the status of flow of a particle suspended sample and a sheath solution inside the flow cell 100 will be explained.

The sample containing suspended particles 160 and the sheath solution flow into the parallel path 150 from the inlet 117. In the parallel flow path 150, the sample and sheath solution flow in according to the shape of the nozzle 114, so that a double fluid layer having an inner layer of the sample and an outer layer of the sheath solution (coated layer) is formed.

The guide 113 of the nozzle 114 suppresses the disturbance of the liquid sample at the nozzle outlet 116. The width of the sample can be kept at almost the width of the guide 113 between the nozzle outlet 116 and the outlet 118. When the ratio of flow rate between the sample and the sheath solution is changed by the guide 113, the width of the sample is kept constant and only the thickness changes.

When a liquid flows into the contraction flow path 151, the liquid is contracted only in the thickness direction and a superflat sample flow with a width of 200 to 300 $\mu$m and a thickness of several to tens $\mu$m is formed.

When the superflat sample flow passes through the measurement flow path 152, the particles 160 in the sample are detected in the particle detection area 80 and imaged in the image picking-up area 90. Then, the superflat sample flow passes through the deceleration flow path 153 and reaches the outlet 118.

In the flow cell 100, the thickness of the superflat sample flow in the measurement flow path 152 is adjusted according to the ratio of flow rate between the sample and the sheath solution. For example, if the flow rate of the sheath solution decreases when the flow rate of the sample is kept constant, the width of the superflat sample flow is kept constant and the thickness thereof increases. If the flow rate of the sheath solution increases, the width of the superflat sample flow is kept constant and the thickness thereof decreases. The particle detector 103 comprises a semiconductor laser source 15, a collimator lens 16, a cylindrical lens 17, a reflecting mirror 18, a minute reflecting mirror 19, a microscope object lens 5, a beam splitter 20, a stop 21, a light detection circuit 22, and a flash lamp lighting control circuit 23. A laser beam from the semiconductor laser source 15 is changed to a parallel laser flux 14 by the collimator lens 16 and the laser flux 14 is focused only in one direction by the cylindrical lens 17. This focused laser flux is irradiated to the particle detection area 80 in the flow cell 100 via the reflecting mirror 18 by the minute reflecting mirror 19 arranged between the microscope lens 3 and the flow cell 100.

The particle detector 103 detects particles according to the particle judgment logic for judging the presence or absence of particles. There are a plurality of particle judgment logics provided. When particles with small diameters are detected, a detection signal from the light detection circuit 22 is on the A level and the judgment logic (algorithm) for judging that particles are detected when the pulse width becomes PA is used. When particles with large diameters are detected, a detection signal from the light detection circuit 22 is on the B level which is different from the A level when small particles are detected and it is judged that particles are detected when the pulse width becomes PB which is different from PA.

In addition to the aforementioned judgment logic, it is possible to use a judgment logic for judging that particles are detected from a change in the waveform of a detection signal from the light detection circuit 22 and to change the judgment level according to the magnitude of the diameter of particles to be measured. When a staining solution is added to a sample solution, it is possible to detect particles by the color level and change the judgment color level according to the magnitude of diameter of particles to be measured.

The particle analyzer 102 converts picture element data signal of an image outputted from the TV camera 8 to a digital signal by the AD converter 24 and stores the data based on it at the predetermined address of the image memory 25 under control of the image processing control circuit 26. The data stored in the image memory 25 is read under control of the image processing control circuit 26 and inputted to the characteristic extraction circuit 27 and the discrimination circuit 28 so as to be image-process ed and the result is supplied to the central control unit 29. The particle classification result and the particle discrimination characteristic parameter data used for particle classification are supplied. The particle classification and discrimination process is automatically executed by the pattern discrimination process which is generally executed based on configurational features relating to configuration, size or color of the particle image. This image processing result, measurement conditions, and processed-image information are sent from the central control unit 29 to the particle number analyzer 40. The particle number analyzer 40 checks the correspondence between the detected particles and the particle classification result on the basis of a particle detection signal from the central control unit 29 and the light detection circuit 22 and a control signal from the image processing control circuit 26 and summarizes the final classification and discrimination result of particle images. The result is returned to the central control unit 29 and outputted and displayed on the display unit 50 when necessary.

On the other hand, to review a particle image, the particle name to be reviewed is inputted by an operator from the key input unit 60 first and transmitted to the discrimination circuit 28 via the central control unit 29. Only when the result classified and discriminated according to biological kind of the particles by the discrimination circuit 28 matches with the set review particle name, is the corresponding particle image sent to the review image memory 30 from the image memory 25 and stored sequentially. As to a particle image, when even a dedicated particle image to be reviewed is a particle image stored in the review image memory 30, it is displayed on the display screen of the display unit 50 for each same particle kind from the review image memory 30 via the central control unit 29 after the sample measurement ends and used for review by the operator.

The particle concentration in the sample and the view field converted particle number are calculated on the basis of these measurement results and the analytical result is returned to the central control unit 29.

A flow system control unit 124 adjusts the ratio of flow rate between a sample and a sheath solution introduced into the flow cell 100 by a signal from the central control unit 29.

Next, the operation of a flow type particle image analytical apparatus of an embodiment of the present invention will be explained.

In FIG. 1, the sample and sheath solution flow in the flow cell 100 from the top of the drawing to the bottom thereof. The laser beam from the semiconductor laser source 15 passes through the collimator lens 16 and is changed to the laser flux 14. The laser flux 14 is irradiated to the flow cell 100 via the cylindrical lens 17 and the reflecting plates 18 and 19. The laser beam passing through the flow cell 100 is reflected from the beam splitter 20 via the microscope object lens 5 and irradiated to the light detection circuit 22 via the stop 21.

When particles in the sample reach the laser beam passing position in the flow cell 100, a detection signal is sent to the particle number analyzer 40 and the flash lamp lighting control circuit 23 from the light detection circuit 22. By this detection signal, the flash lamp lighting control circuit 23 lets the flash lamp 1 light via the flash lamp driving circuit 1a. The flash light from the flash lamp 1 passes through the lens 2 and is irradiated to the particles in the flow cell 100 via the view field stop 11, the aperture stop 12, and the microscope condenser lens 3. An image of the irradiated particles is sent to the TV camera 8 via the microscope object lens 5 so as to be picked up. The image processing control circuit 26 supplies a command signal to the image memory 25 and the particle number analyzer 40 according to this information from the TV camera 8. The image information obtained by the TV camera 8 is supplied to the image memory 25 via the A-D converter 24. The image information is sent to the central control unit 29 from the image memory 25 via the characteristic extraction circuit 27 and the discrimination circuit 28.

The central control unit 29 controls the operations of the particle number analyzer 40, the image processing control circuit 26, and the flow system control unit 124 and lets the display unit 50 display a processed particle image.

To review a particle image, the name of a particle kind to be reviewed is inputted by an operator from the key input unit 60 first before starting sample measurement and transmitted to the discrimination circuit 28 via the central control unit 29. Only when the result classified and discriminated by the discrimination circuit 28 matches with the preset name of review particle kind, is the corresponding particle image sent to the review image memory 30 from the image memory 25 and stored sequentially. The stored particle image is fetched from the review image memory 30 after the sample measurement ends and displayed on the display screen of the display unit 50 for each same particle kind via the central control unit 29. As a review operation for particles, an operator classifies particles finally or changes the classification name by observing a displayed particle image. The review result is transmitted to the central control unit 29 and summarized as a final particle classification result.

According to this embodiment, only images of particles corresponding to the designated particle kind among particles which are automatically classified are stored in the review image memory 30 but all the imaged particles are not stored in the review image memory. Therefore, the review image memory 30 does not require a large memory capacity.

Particle images to be reviewed are displayed on the CRT display screen in batch for each particle kind and hence the review work is simplified.

A large amount of particles of the same kind may be contained in a sample. Under the condition that the automatic particle classification precision of those particles is high, there is no need to designate as review particles for those particles. Under this particle analytical condition, if only particles of kinds other than the above are designated as review particles, remarkable saving of the capacity of the review image memory can be expected.

To classify biological cells, by designating only particles which are important particularly for medical diagnosis as review particles, accomplishment of the measurement object can be expected. The number of such specific particles is small and by designating only specific cells as review particles, the review time can be shortened and the work can be executed simply.

It is possible to switch the measurement mode for one sample and designate the particle kind as a review particle in each switched measurement mode. By doing this, a useless particle image will not be stored in the review image memory. As an actual example of the measurement mode, a case that a sample is measured under the condition of a different flow rate, a case that a sample is measured under the condition of a different image magnification, or a case that a sample is measured under a different particle detection condition (the magnitude of the detection signal level, the pulse width of the signal, etc.) may be cited.

An image of a particle corresponding to the particle kind which cannot be classified by the image process by the apparatus may be stored in the review image memory 30. In this case, such a particle which cannot be classified can be classified by the particle image review function by watching the image by an operator and improvement of the classification and discrimination precision can be expected.

A review flow chart of a particle image which cannot be classified as mentioned above is shown in FIG. 3. With reference to the drawing, whether the normal process is switched to the storing process of an image of a particle which cannot be classified or not, that is, the storing process of the latter is turned on or off is designated first (S1). In the drawing, it is described simply as "process switching on/off". Next, the particle kind to be reviewed is designated (S2), and then a particle is detected as usual, and an image of the detected particle is inputted (S3) and processed so as to extract a characteristic parameter (S4), and also the particle classification and discrimination process is executed by the pattern recognition process (S5). Thereafter, whether the image is an image of a particle corresponding to the particle kind designated to be reviewed or not is judged (S6). When the result is yes, the particle image and classification result are stored in the review image memory (S7). Even if the image is not an image of a particle corresponding to the designated particle kind, whether the image storage at Step S1 is in the ON state or not is judged (S8). Furthermore, only when the answer is yes, whether the corresponding particle image is an image of a particle which cannot be classified or not is judged (S9). When the answer is yes, the image and classification result are stored in the review image memory. By doing this, it is found that when a particle cannot be classified, the image thereof and classification result are stored in the review image memory regardless of whether the particle is a particle corresponding to the particle kind designated to be reviewed.

Thereafter, the calculation for each classification is executed (S10) and whether the processing is completed or not is judged (S11). When the processing ends, the review work for the review particle is executed. Namely, whether the corresponding particle is a review particle or not is judged (S12). When the answer is yes, the image of the particle corresponding to the designated particle kind is displayed and the review work is executed by observing the image (S13). Needless to say, data is corrected if necessary. Then, undesignated review particles are also displayed and reviewed and data is corrected if necessary (S14). Finally, whether the review work ends or not is judged (S15). When the review work ends, the final classification result which is reflected by the review result is outputted (S16).

As to an image of an ambiguous particle which is considered to correspond to the particle kind of the first candidate but is considered to possibly correspond to the particle kind of the second candidate close to the particle kind of the first candidate, it is possible to store it in the review image memory. This particle image can be reviewed almost in the same way as that shown in FIG. 3. The reason is that if Step S1 is considered as a step of designating whether the storage of an image of an ambiguous particle is turned on or off and Step S9 is considered as a step of judging whether the corresponding particle is close to the particle kind of the second candidate or not, the flow shown in FIG. 3 can be used as a flow for reviewing an ambiguous particle. Therefore, the explanation of review of an ambiguous particle by referring to FIG. 3 will be omitted so as to avoid duplication.

For an ambiguous particle, it is desirable to display the particle kind names of the two candidates in addition to the image of the particle from a viewpoint of improving the efficiency of the classification work.

Figure 3:
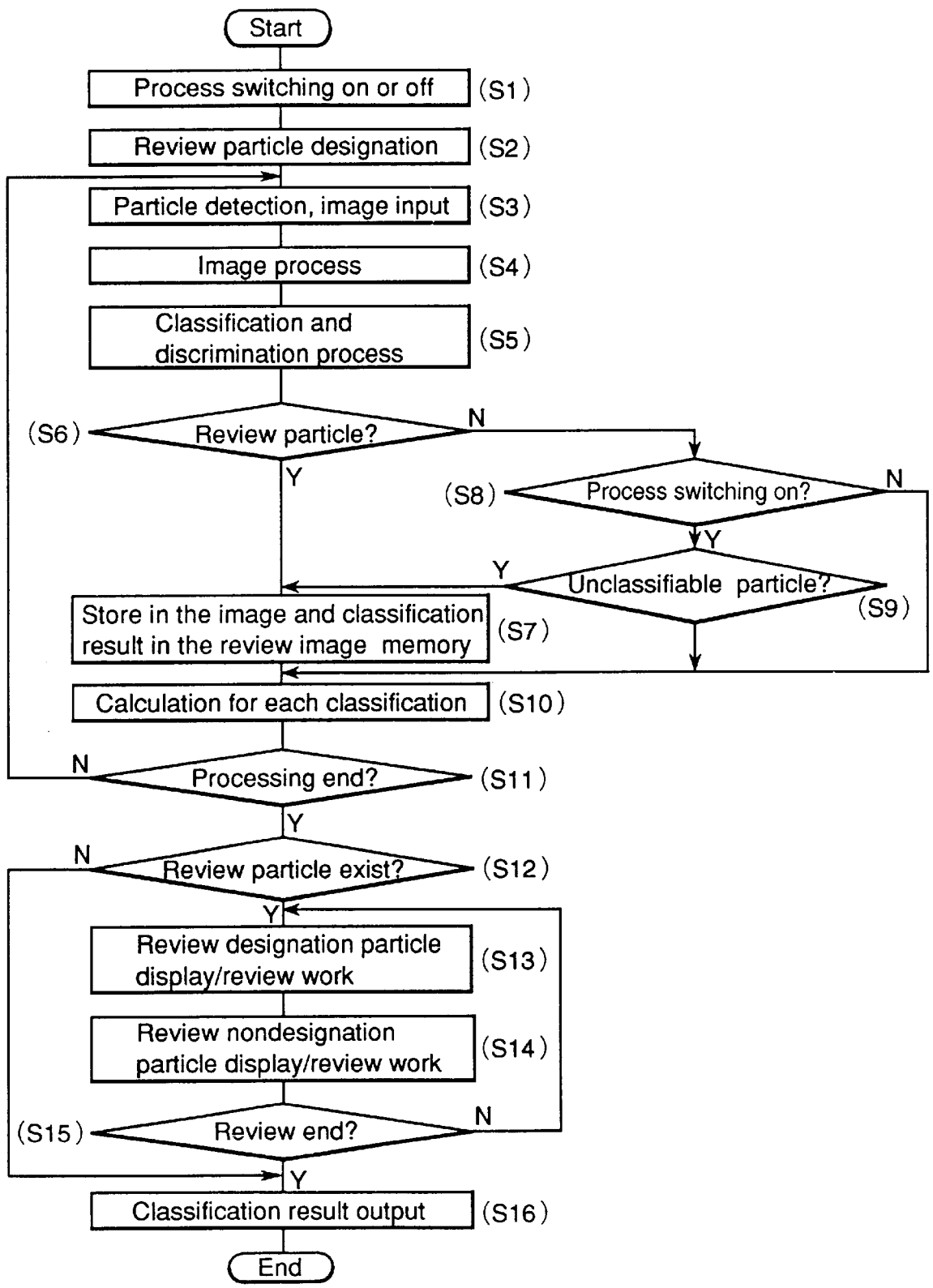
FIG. 3 is a flow chart for the review work as an example used together with the apparatus shown in FIG. 1.

As to a particle corresponding to another particle kind which is apt to be misdecided as one corresponding to the designated particle kind by automatic classification, it is possible to store it in the review image memory. Also in this case, the particle can be reviewed almost in the same way as that shown in FIG. 3. The reason is that if Step S1 shown in FIG. 3 is considered as a step of designating whether the storage of an image of a particle corresponding to another particle kind which is apt to be misdecided as one corresponding to the designated particle kind is turned on or off and Step S9 is considered as a step of judging whether the corresponding particle is a particle which is apt to be misdecided or not, the flow shown in FIG. 3 can be substituted for a flow for reviewing the particle. Therefore, the explanation of review of the particle by referring to FIG. 3 will be omitted so as to avoid duplication.

Figure 4:
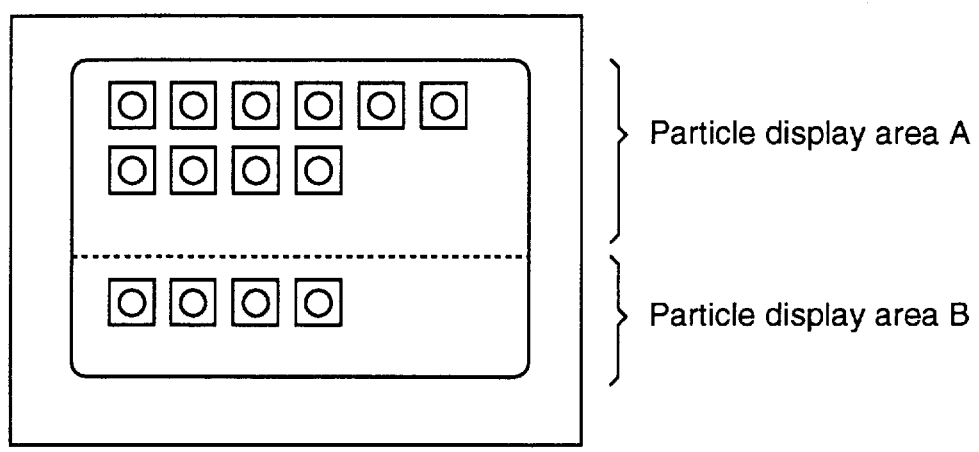
FIG. 4 shows a display screen of review images of the display unit shown in FIG. 1 as an example.

For particles which are apt to be misdecided as mentioned above, it is desirable to display an image of a particle corresponding to the particle kind which is originally designated and a fixed number of images of particles corresponding to another particle kind which is apt to be misdecided at positions close to each other so as to allow mutual comparison observation. FIG. 4 shows a display example of an actual review image of the display unit 50 in that case.

In FIG. 4, images of particles corresponding to the particle kind designated as a review particle are displayed in the particle display area A and images of particles corresponding to a particle kind which is apt to be misdecided are displayed in the particle display area B. By doing this, an operator can proceed with the classification work of the particles efficiently by comparing and observing the images displayed in both the display areas. Needless to say, when he classifies particles finally through the classification review work or changes the particle kind name, the automatic classification result which is reflected and corrected by the result is outputted. Therefore, by doing this, the particle classification and discrimination precision can be improved.

To classify biological cells, particularly as to a particle kind which is important for medical diagnosis, it is significant to decide it as a specific particle kind, register it in the memory inside the central control unit 29, and store it in the review image memory when the storage is in the ON state. The reason is that there is no need to designate each time.

Also in this case, particles can be reviewed almost in the same way as that shown in FIG. 3. The reason is that if Step S1 shown in FIG. 3 is considered as a step of designating whether the storage of an image of a particle corresponding to the specific particle kind is turned on or off and Step S9 is considered as a step of judging whether the corresponding particle is the specific particle or not, the flow shown in FIG. 3 can be substituted for a flow for reviewing the particle. Therefore, the explanation of review of the particle by referring to FIG. 3 will be omitted so as to avoid duplication.

When there are many particles stored in the review image memory and the capacity of the review image memory is not sufficient, it is desirable to correct the automatic classification result by the particle existence ratio of reviewed particle images. The reason is that by doing this, even if the memory capacity becomes insufficient, the classification and discrimination precision will not be lowered.

Figure 5:
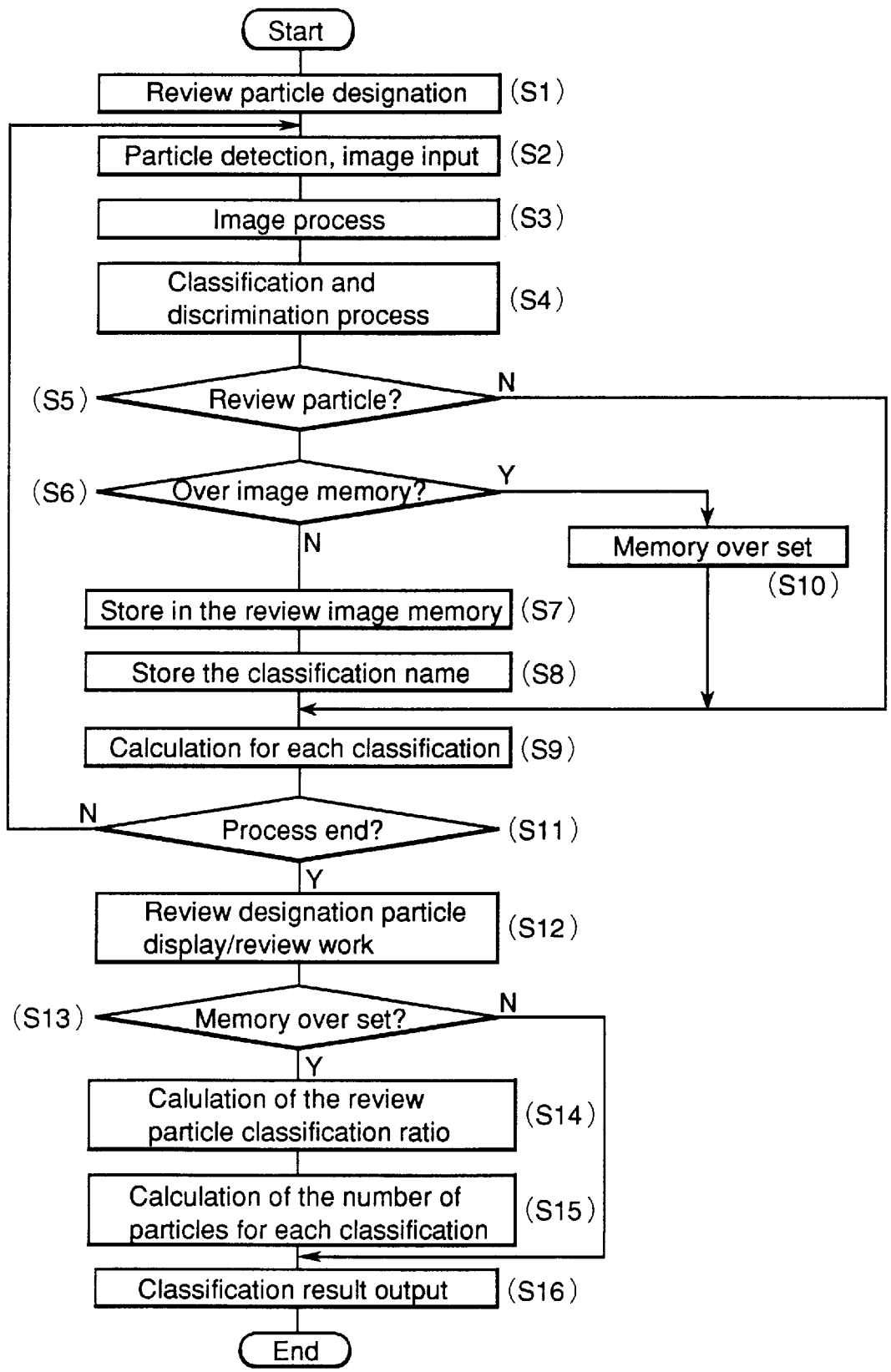
FIG. 5 is a flow chart for the review work as another example used together with the apparatus shown in FIG. 1.

The flow of this work will be explained by referring to FIG. 5. When the particle image analysis starts, the review particle is designated first (S1), and then the particle detection and image input (S2), the characteristic parameter extraction by image processing (S3), and the particle classification and discrimination process by pattern recognition (S4) are executed as in the above explanation. When it is judged next at Step S5 that the review particle is designated and it is furthermore judged at Step S6 that the review image memory is not over the capacity thereof, the image of the particle is stored in the review image memory (S7), and the particle kind name thereof is also stored (S8) in it, and the calculation for each classification is executed (S9).

However, the capacity of the review image memory is limited and there may be a case that images of all review candidate particles cannot be stored fully. If this occurs, "memory over" is set (S10) and the storage of images into the review image memory is stopped. The aforementioned series of operations is continued for one sample and when the processing ends (S11), the review operation is started.

As to the review operation, an image of the review-designated particle is displayed on the display unit and the classification result is classified again or finally by an operator (S12). Next, when "memory over" is set (S13), the existence (classification) ratio is calculated for each classification of a particle corresponding to the review-designated particle kind (S14). Finally, the whole particle classification result is calculated in consideration of the classification ratio of review particles obtained by the review operation for all the designated particles (S15) and the result is outputted (S16).

As a particle detection means, a case where a laser flux from a semiconductor laser is used as detection light and the laser flux scattered by particles is used, is described. However, there is no limit to it. Fluorescence from particles or transmitted light may be used, or a method for detecting particles by a one-dimensional image sensor or a method for detecting particles by a change in the electric resistance due to passage of particles may be used.

In the embodiment, a flow cell keeping the width of a sample constant is used. However, the present invention can be applied to an apparatus using a flow cell for enlarging or reducing the width of a sample slowly in the imaging area.

Effects of the present invention are as follows:

1. The present invention designates the kind of particles to be reviewed, controls storage of an image in a review image memory so as to store an image of particles corresponding to the designated particle kind in the review image memory, and displays the stored particle image on the display for review, so that all generated particle images are not always stored in the review image memory. Accordingly the memory capacity can be minimized and since there is no need to reduce the number of review particles to be stored originally regardless of it, the reproducibility of the classification result can be prevented from reduction.

2. The present invention displays particle images in batch for each particle kind, so that the review work can be simplified.

3. The present invention designates the particle kind for one sample in each measuring mode, so that useless particle images can be prevented from storage in the review image memory.

4. The image storage control means includes a means for turning storage of an image of particles which cannot be classified on or off and is structured so as to store the image of particles which cannot be classified in the review image memory when the image storage ON/OFF means is in the ON state, so that particles which cannot be classified by the apparatus can be classified by an operator.

5. The present invention has a means for registering a specific particle kind beforehand and the image storage control means includes a means for turning storage of an image of particles corresponding to the specific particle kind on or off and is structured so as to store an image of particles which correspond to the registered specific particle kind and are automatically classified in the review image memory when the image storage ON/OFF means is in the ON state, so that when, for example, particularly particles which are medically important are selected as a specific particle, these particles can be reviewed by an operator even if they are not designated one by one.

6. The image storage control means includes a means for turning storage of an image of ambiguous particles which are considered to correspond to the particle kind of the first candidate but are considered to possibly correspond to the particle kind of the second candidate close to the particle kind of the first candidate, on or off and is structured so as to store the image of ambiguous particles in the review image memory when the image storage ON/OFF means is in the ON state and the display means is structured so as to display the particle kinds of both the candidates in addition to the image of ambiguous particles which is stored as an image relating to the particle kinds of both the candidates, so that ambiguous particles which cannot be classified definitely by the apparatus can be classified efficiently by review by an operator.

7. The image storage control means includes a means for turning storage of an image of particles on or off and is structured so as to store an image of particles corresponding to another particle kind which is apt to be misdecided as one corresponding to the designated particle kind by automatic classification in the review image memory when the image storage ON/OFF means is in the ON state and the display means is structured so as to display the image of particles corresponding to the designated particle kind and the image of particles corresponding to the another particle kind for comparison observation, so that particles which cannot be classified correctly by the apparatus can be classified efficiently by an operator.

8. The present invention is structured so that an operator classifies particles displayed on the display unit finally or changes the particle kind name and furthermore corrects the automatic classification result of particles which are automatically classified on the basis of the aforementioned classification result, so that the particle classification and discrimination precision can be improved.

9. The present invention is structured so that the automatic classification result of the automatically classified particles is corrected on the basis of the existence ratio of the particles which are objects of review for each corresponding particle kind, so that even if the capacity of the review image memory is insufficient, the particle classification and discrimination precision can be prevented from reduction due to it.

What is claimed is:

1. A flow type particle image analytical apparatus having a forming means for forming a sample flow by flowing a sample liquid containing particles, a generating means for generating images of said particles in said sample liquid by irradiating light to said sample flow, and an automatic classifying means for classifying information relating to said particles obtained by analyzing said images detected based on plural configurational features relating to configuration, size or color of the image, wherein said apparatus further comprises a selecting means for selecting at least one to be reviewed of the particles, as to which information has been classified, a review image memory for storing an image of said particles corresponding to said selecting, a display means for displaying said image stored in said review image memory for reviewing said image, whereby said information relating to said particles which are selected and are not selected to be reviewed is corrected based on said image stored in said review image memory, a registering means for registering a specific particle kind beforehand, and an image storage control means including an image storage ON/OFF means for setting ON/OFF of storage of an image of said particles corresponding to said specific particle kind and storing said image of said particles which correspond to said specific particle kind and are automatically classified, in said review image memory when said image storage ON/OFF means is in the ON state.

2. A flow type particle image analytical apparatus according to claim 1, which further comprises an image storage control means including a means for setting ON/OFF of storage of an image of ambiguous particles which are considered to correspond to a particle kind of a first candidate but are considered to possibly correspond to a particle kind of a second candidate close to said particle kind of said first candidate and for storing said image of said ambiguous particles in said review image memory, when said image storage ON/OFF means is in the ON state, and wherein said display means is structured so as to display said kinds of both said candidates in addition to said image of ambiguous particles which is stored as an image relating to said particle kinds of both said candidates.

3. A flow type particle image analytical apparatus according to claim 1, which further comprises an image storage ON/OFF means for setting ON/OFF of storage of an image of said particles and storing an image of particles corresponding to another particle kind which is apt to be misdecided as one corresponding to said designated particle kind by automatic classification in said review image memory when said image storage ON/OFF means is in the ON state, and wherein said display means is structured so as to display said image of particles corresponding to said designated particle kind and said image of particles corresponding to said another particle kind for comparison observation.

4. A flow type particle image analytical apparatus according to claim 1, wherein said particles are displayed on the display unit and finally classified or the particle kind name thereof is changed and furthermore said automatic classification result of particles which are automatically classified is corrected on the basis of said classification result.

5. A flow type particle image analytical apparatus according to claim 4, wherein said automatic classification result of said automatically classified particles is corrected on the basis of the existence ratio of said particles for each corresponding particle kind.

6. A flow type particle image analytical apparatus according to claim 1, wherein said particles are cells of an organism.

7. A flow type particle image analytical apparatus according to claim 1, wherein said particles are blood corpuscles in blood.

8. A flow type particle image analytical apparatus according to claim 1, wherein said particles are sediment of urine.

* * * * *